United States Patent
Radford et al.

(10) Patent No.: US 10,648,730 B1
(45) Date of Patent: May 12, 2020

(54) MEDICAL IMPLEMENT DRYING APPARATUS

(71) Applicant: Cenorin, LLC, Kent, WA (US)

(72) Inventors: Drew R. Radford, Seattle, WA (US); Paul Leung, Bellevue, WA (US)

(73) Assignee: Cenorin, LLC, Kent, WA (US)

( * ) Notice: Subject to any disclaimer, the term of this patent is extended or adjusted under 35 U.S.C. 154(b) by 78 days.

(21) Appl. No.: 15/974,414

(22) Filed: May 8, 2018

Related U.S. Application Data

(60) Provisional application No. 62/503,148, filed on May 8, 2017.

(51) Int. Cl.
  *F26B 3/02* (2006.01)
  *A61B 90/70* (2016.01)
  *A61B 1/12* (2006.01)

(52) U.S. Cl.
  CPC ............... *F26B 3/02* (2013.01); *A61B 1/123* (2013.01); *A61B 90/70* (2016.02)

(58) Field of Classification Search
  CPC ...... F26B 3/02; F26B 5/00; F26B 9/00; F26B 9/06; F26B 5/04; F26B 3/20; F26B 11/00; F26B 21/00; A61B 90/70; A61B 1/123
  USPC ........................................................ 34/201
  See application file for complete search history.

(56) References Cited

U.S. PATENT DOCUMENTS

| | | | | |
|---|---|---|---|---|
| 5,659,977 A | * | 8/1997 | Jensen | A01G 33/00 34/547 |
| 5,974,689 A | * | 11/1999 | Ferrell | B08B 3/04 134/21 |
| 6,223,455 B1 | * | 5/2001 | Chickering, III | B01J 2/04 34/578 |
| 7,966,746 B2 | * | 6/2011 | Py | F26B 5/06 34/413 |

(Continued)

FOREIGN PATENT DOCUMENTS

| DE | 102014111319 A1 | 2/2016 |
|---|---|---|
| EP | 2837352 A1 | 2/2015 |

(Continued)

OTHER PUBLICATIONS

Intuitive Surgical, "EndoWrist Instruments Reprocessing Wall Chart, Used in conjunction with the Intuitive Surgical da Vinci S and da Vinci Si Surgical Systems", 2014, 1 page.

(Continued)

*Primary Examiner* — Stephen M Gravini
(74) *Attorney, Agent, or Firm* — Schacht Law Office, Inc.; Dwayne Rogge

(57) ABSTRACT

Disclosed herein is a novel medical implement drying apparatus and a method for holding and drying certain medical implements during a reprocessing sequence. This is accomplished by forcing air through the apparatus. The apparatus and method disclosed herein is useful for many medical implements having a hollow casing. The medical implement drying apparatus is particularly well suited for use with a drying cabinet containing one or more of the (Continued)

medical implements during the drying process which will facilitate drying of the exterior of each medical implement, while the disclosed apparatus removes water and water vapor from the interior of each medical implement. Specialized holders, racks, and drying gas pumping systems are also disclosed.

17 Claims, 8 Drawing Sheets

(56) References Cited

U.S. PATENT DOCUMENTS

| | | |
|---|---|---|
| 8,206,406 B2 | 6/2012 | Orban |
| 8,407,912 B2 * | 4/2013 | Hubbard, Jr. ............. F26B 3/12 34/82 |
| 8,429,831 B2 * | 4/2013 | Gillick .................. F26B 21/004 34/78 |
| 10,377,520 B2 * | 8/2019 | Root ........................ A61M 5/14 |
| 2011/0017244 A1 * | 1/2011 | Lau ..................... C23C 16/0236 134/105 |
| 2016/0242868 A1 | 8/2016 | Robert et al. |

FOREIGN PATENT DOCUMENTS

| | | |
|---|---|---|
| EP | 2837353 A1 | 2/2015 |
| JP | 2016202746 A | 12/2016 |
| WO | 2012148266 A1 | 11/2012 |

OTHER PUBLICATIONS

Intuitive Surgical, Inc., "The da Vinci Surgical System", http://www.daVinciSurger.com; 2016, 3 pages.

* cited by examiner

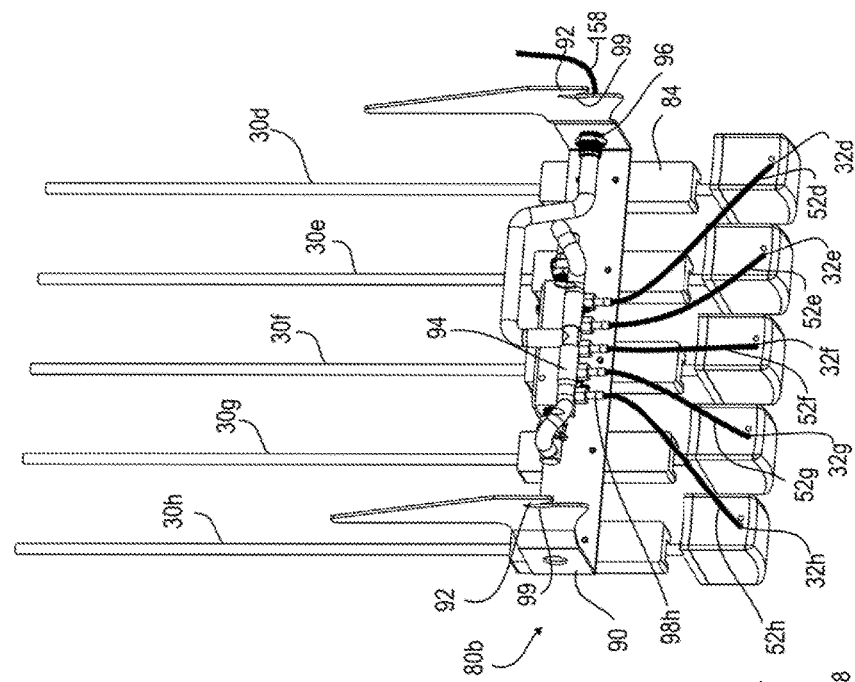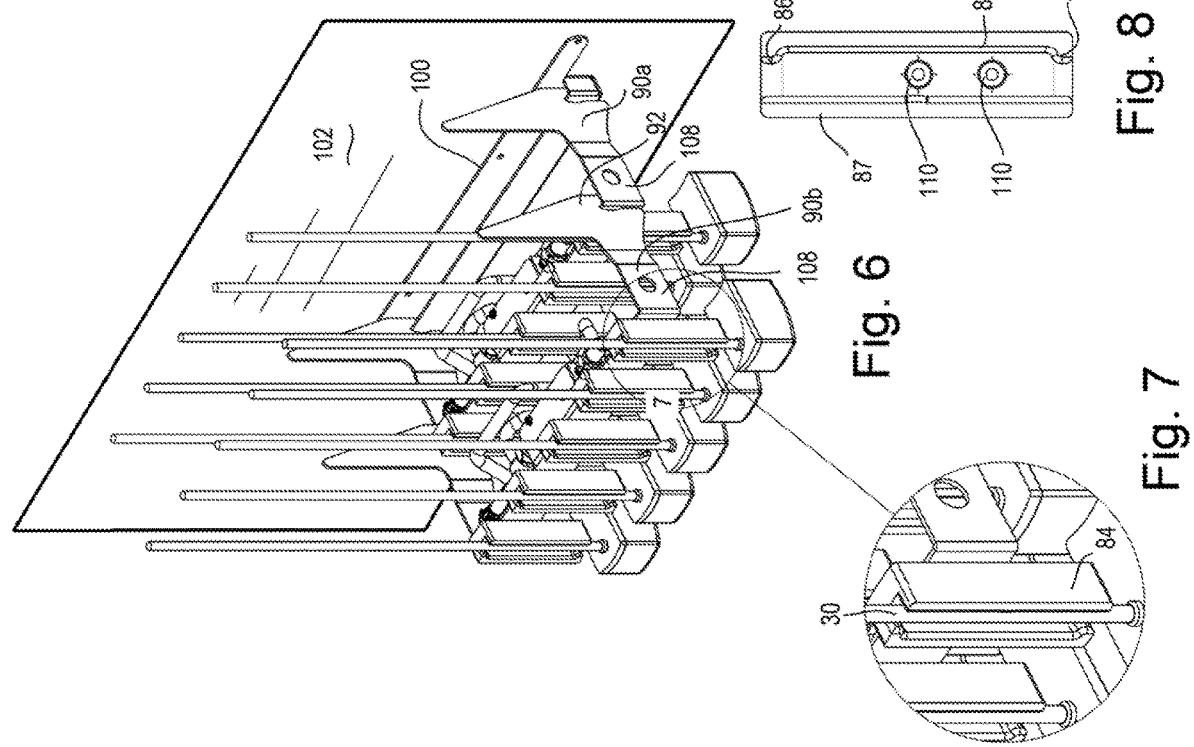

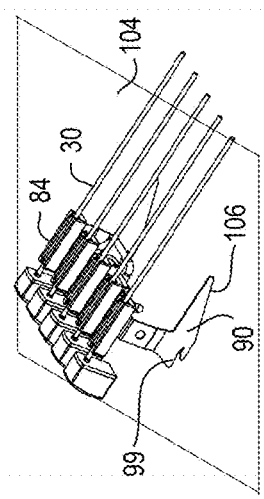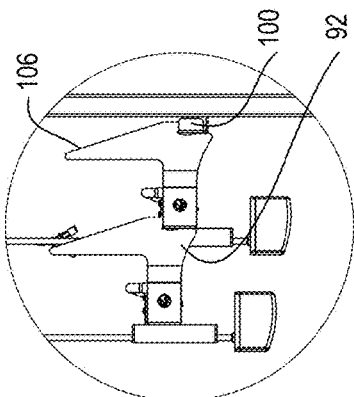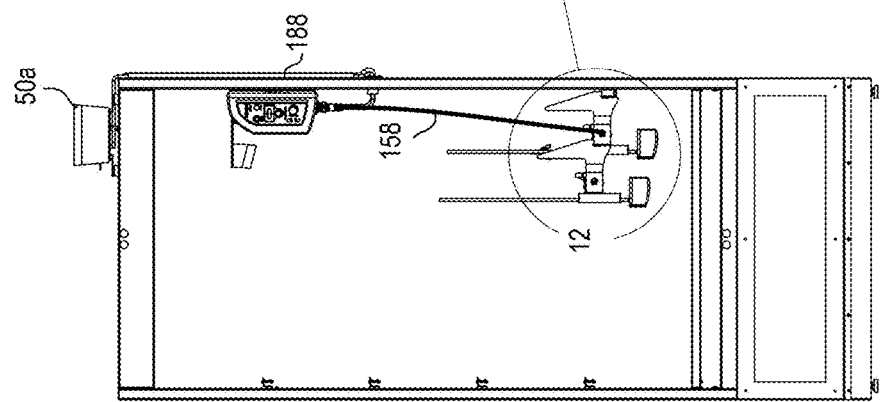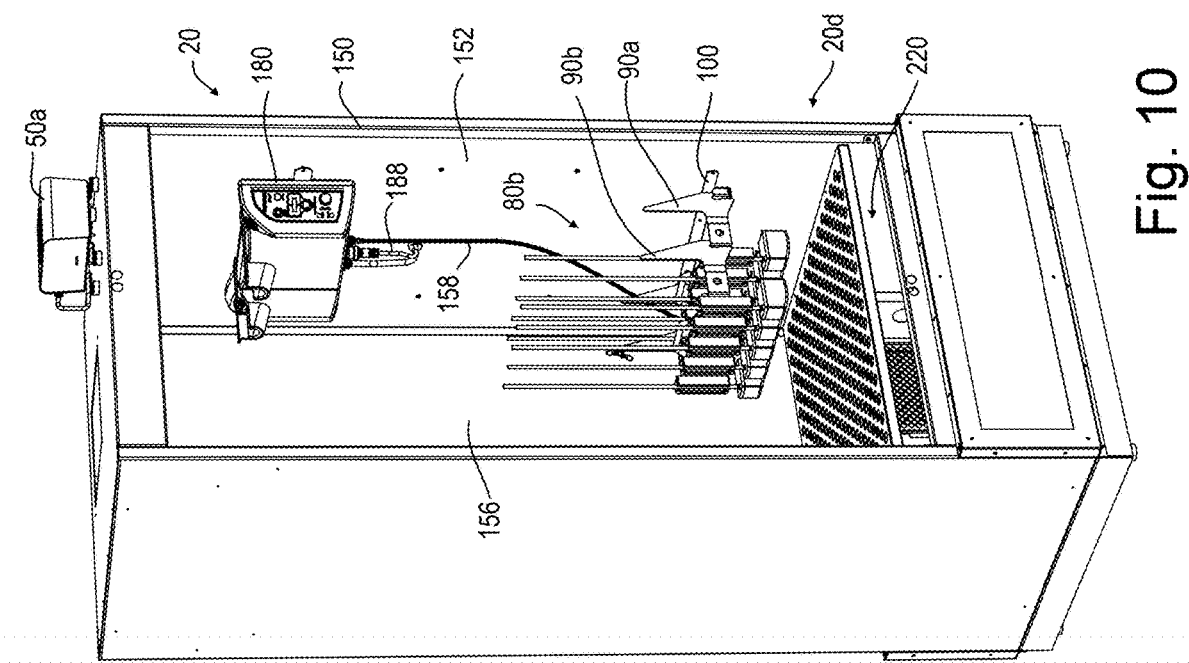

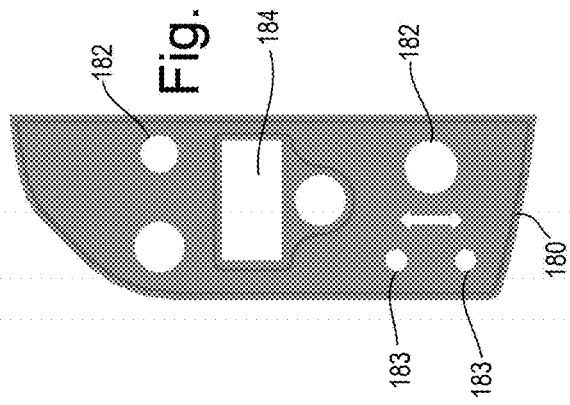
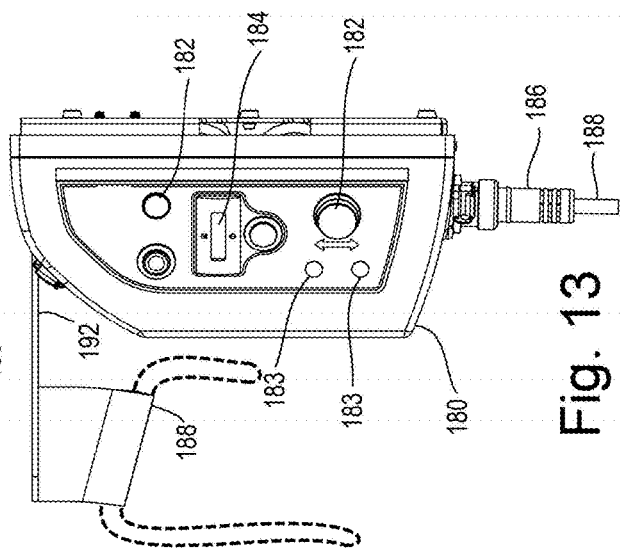
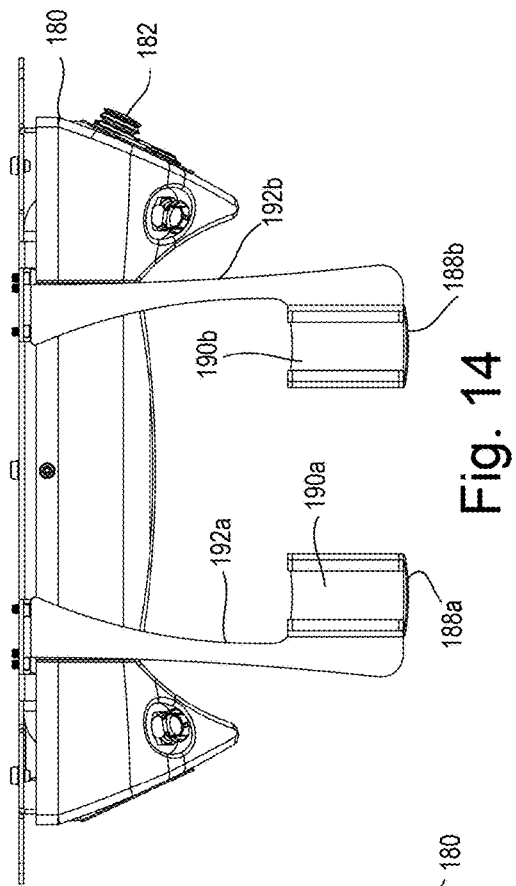
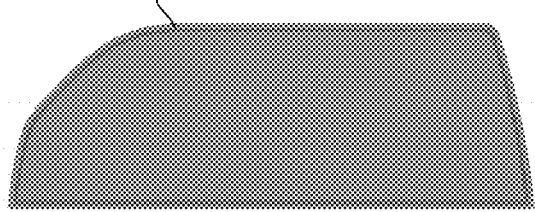
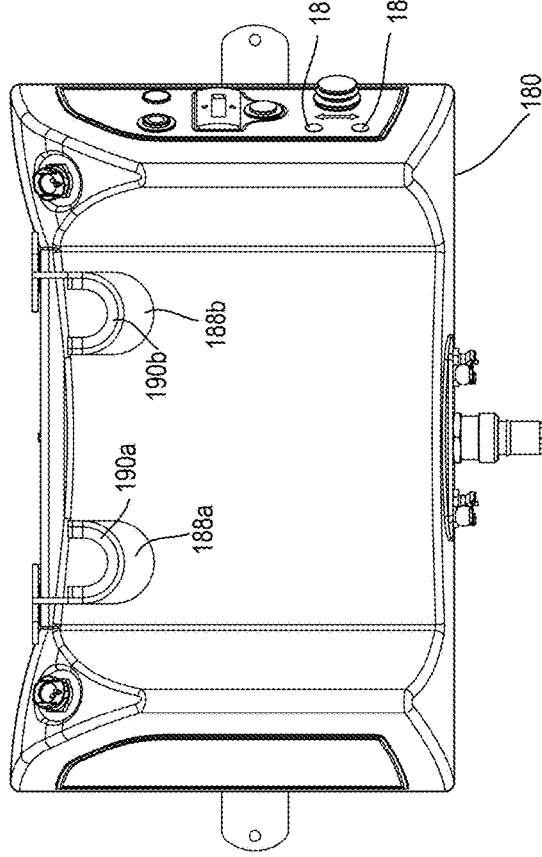

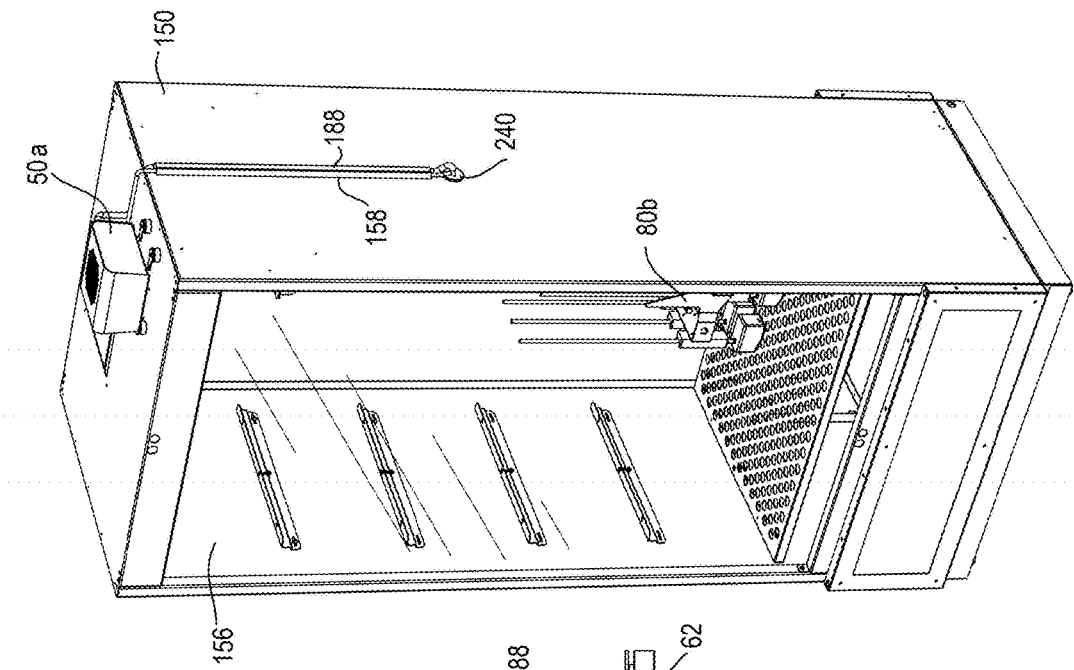
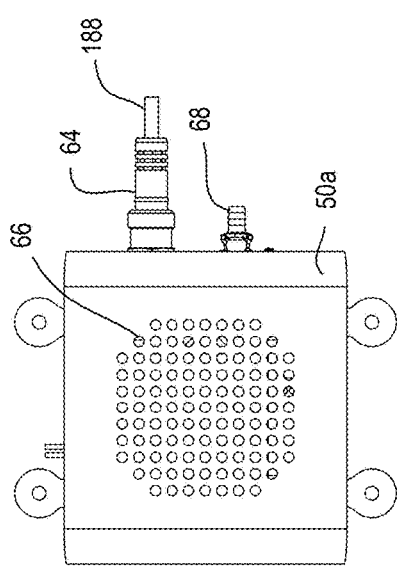
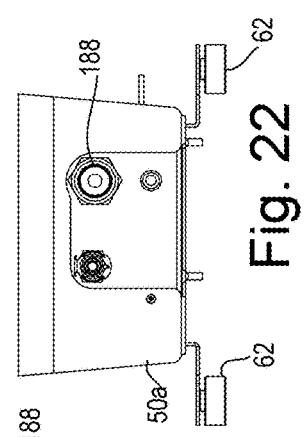
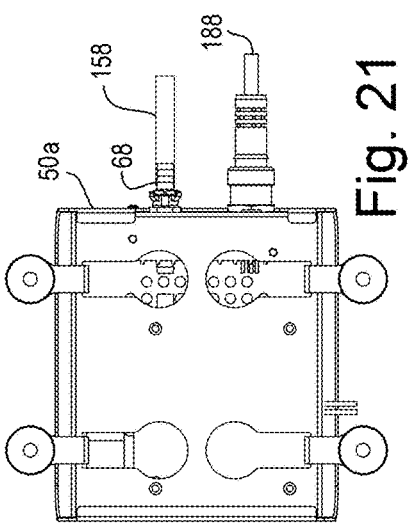
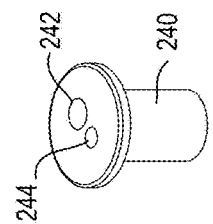
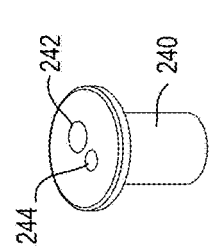

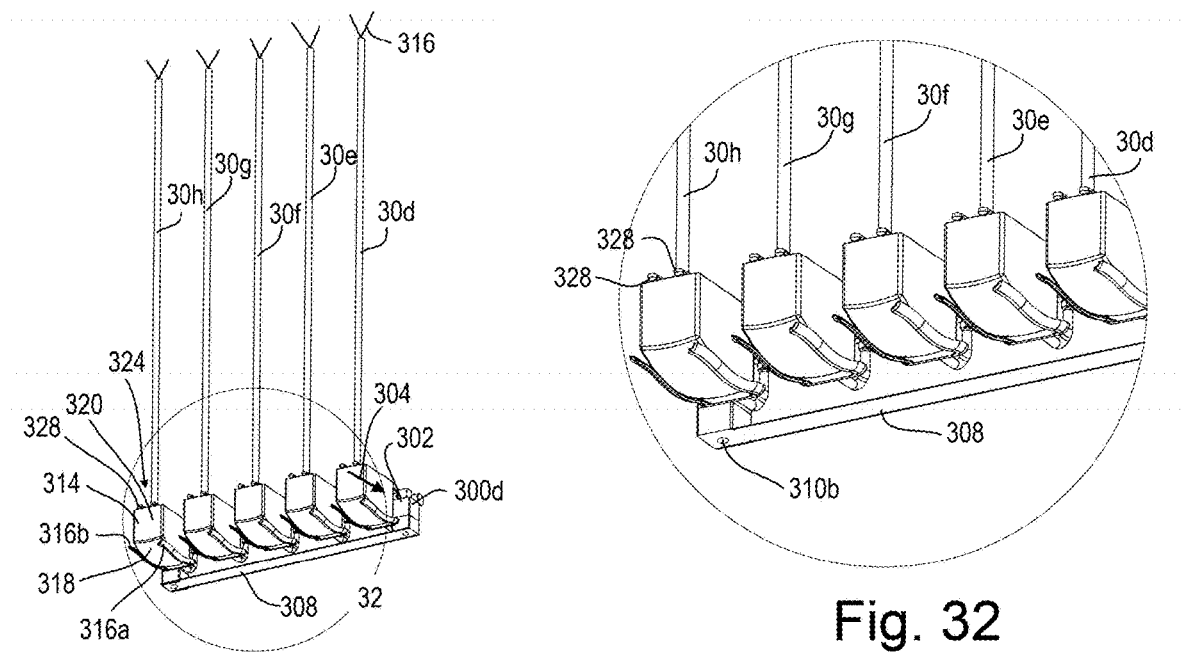
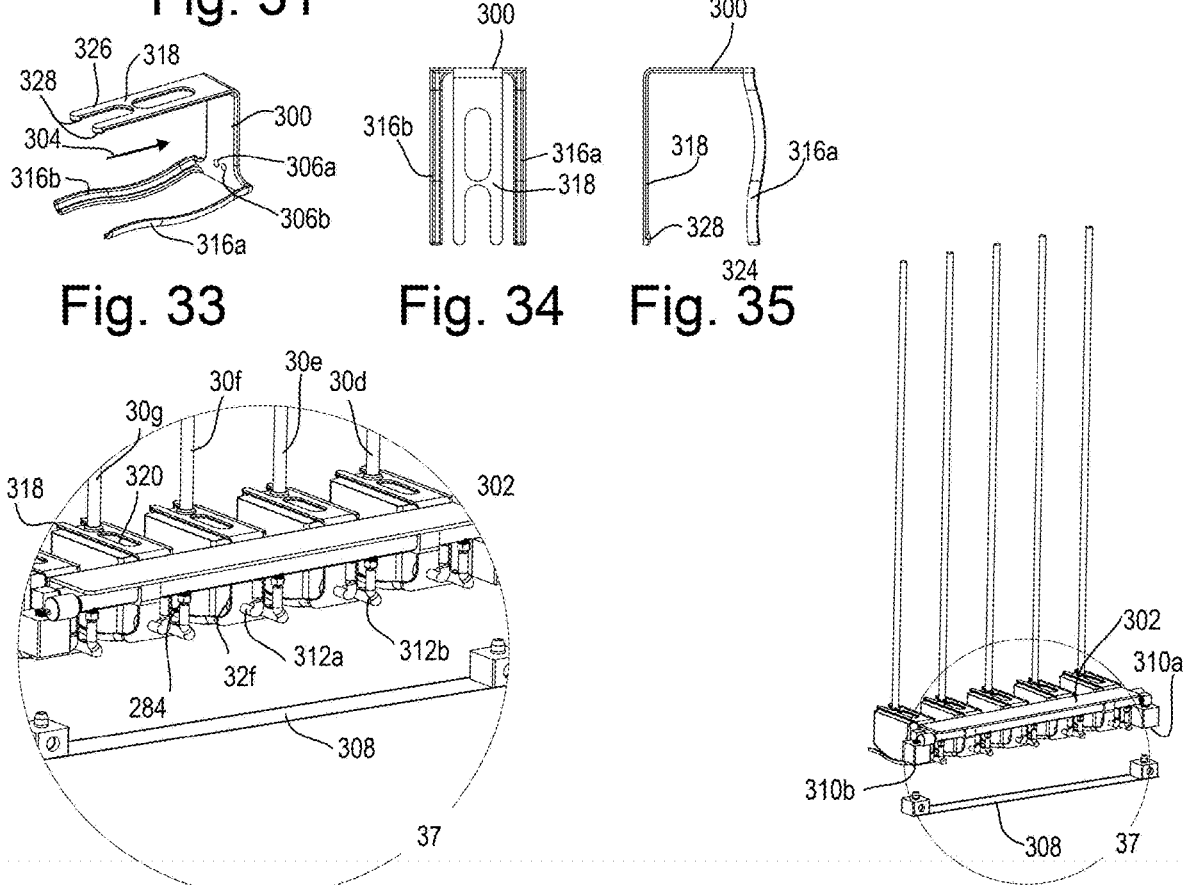
Fig. 31
Fig. 32
Fig. 33
Fig. 34
Fig. 35
Fig. 36
Fig. 37

MEDICAL IMPLEMENT DRYING APPARATUS

RELATED APPLICATIONS

This application claims priority benefit of U.S. Ser. No. 62/503,148, filed May 8, 2017, incorporated herein by reference.

BACKGROUND OF THE DISCLOSURE

Field of the Disclosure

This application relates to the field of drying apparatuses for repurposing of medical implements having a hollow or partially hollow outer shell with airflow therethrough.

BRIEF SUMMARY OF THE DISCLOSURE

Disclosed herein is a medical implement drying apparatus comprising in one example: a drying gas pump; at least one gas conduit having a first end fluidly coupled to the drying gas pump with a second end fluidly coupled to a medical implement having an enclosed interior space. The term fluid including both gasses and liquids. The medical implement of one example having an inlet port coupled to the gas conduit in fluid communication with the interior space. The medical implement in one example having an outlet port in fluid communication with the interior space; and wherein drying gas is forced from the drying gas pump, through the gas conduit, absorbs water and water vapor within the medical implement, exits the medical implement via the outlet port, and thus carries water and water vapor out of the interior space.

The medical implement drying apparatus may further comprise: a gas manifold having an inlet coupled to the drying gas pump and a plurality of manifold outlets; each manifold outlet coupled to at least one of the gas conduits; a plurality of the medical implements; and each medical implement coupled to the gas manifold via at least one of the gas conduits.

The medical implement drying apparatus in one example may further comprise an implement rack. The implement rack comprising a plurality of attachment locations; and each attachment location configured to removably hold a medical implement.

The medical implement drying apparatus may further comprise: a gas manifold having an inlet coupled to the drying gas pump and a plurality of manifold outlets; each manifold outlet coupled to at least one of the gas conduits; a plurality of the medical implements; each medical implement coupled to the gas manifold via at least one of the gas conduits; and wherein the manifold outlet is fixed to the implement rack and removably coupled to the drying gas pump.

The medical implement drying apparatus may also comprise: a bracket fixed to a support structure; and the implement rack removably attached to the bracket.

The medical implement drying apparatus may be arranged wherein the implement rack comprises: a first implement holder assembly comprising a plurality of the attachment locations; the first implement holder assembly removably supported by the bracket; and a second implement holder assembly comprising a plurality of the attachment locations; the second implement holder assembly removably supported by the first implement holder assembly.

The medical implement drying apparatus may be arranged wherein each implement holder assembly comprises: a gas manifold having an inlet coupled to the drying gas pump and a plurality of manifold outlets; each manifold outlet coupled to at least one of the gas conduits; a plurality of the medical implements; and each medical implement coupled to the gas manifold via at least one of the gas conduits.

The medical implement drying apparatus may be arranged wherein each implement holder assembly comprises: a loading surface wherein the loading surface is configured on a horizontal surface in a loading orientation as medical implements are removably held by the implement holder; and a bracket attachment surface configured to attach the implement holder to the bracket without tools in a holding orientation.

The medical implement drying apparatus may be arranged wherein the loading orientation is substantially orthogonal to the holding orientation in a vertical plane.

The medical implement drying apparatus may further comprise: a substantially enclosed cabinet housing the drying gas pump, each gas conduit, each medical implement; the drying gas pump external of the cabinet; and a supply conduit in fluid communication with the drying gas pump and each gas conduit.

The medical implement drying apparatus may further comprise a drying apparatus configured to reduce the humidity within the cabinet.

The medical implement drying apparatus may further comprise a control interface mounted to the cabinet wherein the control interface comprises switches configured to control airflow through the supply conduit.

The medical implement drying apparatus may be arranged wherein the control interface comprises a timer visually observable to an operator.

The medical implement drying apparatus may be arranged wherein the drying gas pump has in inlet port exterior of the cabinet and is not fluidly coupled to the interior thereof.

BRIEF DESCRIPTION OF THE SEVERAL VIEWS OF THE DRAWINGS

FIG. 2 is a highly schematic view of the medical implement shown in

FIG. 1 attached to a gas source via a conduit.

FIG. 5 is a perspective view of one example of an implement holder component in use in an apparatus drying the plurality of medical implements.

FIG. 6 is a perspective view of a plurality of interconnected holder components shown in FIG. 5.

FIG. 7 is an enlarged view of the region 7 of FIG. 6.

FIG. 8 is an enlarged view of one example of a coupling component of the holder component shown in FIG. 7.

FIG. 9 is a perspective view of the example shown in FIG. 5 in a horizontal or loading orientation.

FIG. 10 is a perspective view of one example of a cabinet housing several components including the apparatus shown in FIG. 6.

FIG. 11 is a front view of the example shown in FIG. 10.

FIG. 12 is an enlarged view of the region 12 of FIG. 11.

FIG. 13 is a front view of one example of a control interface component shown in FIG. 10.

FIG. 14 is a top view of the control interface shown in FIG. 13.

FIG. 15 is a rear view of the control interface shown in FIG. 13.

FIG. 16 is a side view of the control interface shown in FIG. 13.

FIG. 17 is a front view of the control interface shown in FIG. 13.

FIG. 18 is a side hidden line view of the control interface shown in

FIG. 13.

FIG. 19 is a top view of one example of a drying gas source component shown in FIG. 10.

FIG. 20 is a side view of the gas pump component shown in FIG. 19.

FIG. 21 is a bottom view of the gas source component shown in FIG. 19.

FIG. 22 is a rear view of the gas source component shown in FIG. 19.

FIG. 23 is a perspective view of a grommet component shown in

FIG. 10.

FIG. 24 is a perspective view of the example shown in FIG. 10.

FIG. 31 is a perspective view of another example of an implement holder with a plurality of medical implements held thereon.

FIG. 32 is an enlarged view of the region 32 of FIG. 31.

FIG. 33 is a perspective view of another example of a coupling device.

FIG. 34 is a bottom view of the coupling device shown in FIG. 33.

FIG. 35 is a side view of the coupling device shown in FIG. 33.

FIG. 36 is a rear perspective view of the example shown in FIG. 31.

FIG. 37 is an enlarged view of the region 37 of FIG. 36.

DETAILED DESCRIPTION OF THE DISCLOSURE

Disclosed herein is a novel medical implement drying apparatus 20 (with specific examples 20a-20d shown in FIGS. 2-4, and 10) with a device and a method for holding and drying certain medical implements 30 during a reprocessing sequence. The apparatus and method disclosed herein is useful for many medical implements having a hollow casing, lumen, hollow tube, or other substantially enclosed inner space.

The medical implement drying apparatus 20 disclosed herein is particularly well suited for use with a drying cabinet 150 containing one or more of the medical implements during the drying process. The drying cabinet configured for drying of the exterior of each medical implement 30, while the disclosed apparatus removes water and water vapor from the inner space of each medical implement 30.

The apparatus and method disclosed herein is particularly well-suited to the drying of medical implements 30 such as robotic assemblies used in remote surgical processes. Such devices having a hollow casing, lumen, hollow tube, or other substantially enclosed inner space enclosed by a casing which also substantially encases moving and possibly electronic components. This combination resulting in an irregular inner space generally prone to pooling of fluids and contaminates which then may be passed on to a subsequent patient, causing infection. One example of such medical implements 30 being the endoscope and endowrist implements used with robotic surgical systems.

Figure 1:
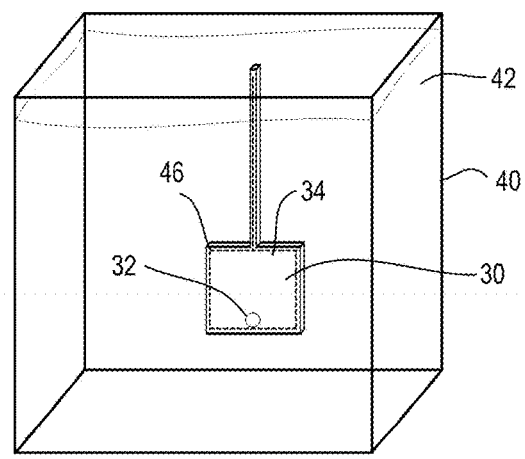
FIG. 1 is a highly schematic view of a partially hollow medical implement held within a container partially filled with cleaning fluid.

In particular, testing has been conducted with implements of the Sa Vinci™ surgical system with the disclosed system providing superior drying and repeatability over known drying processes. A highly schematic version of the exterior of one such a medical implement 30 is shown in FIG. 1.

Reusable medical devices are devices that health care providers can use more than once to treat multiple patients, or to treat the same patient more than once. Often cleaning and disinfecting or reprocessing steps are required between patients, or between uses. Examples of reusable (reprocessable) medical devices include surgical instruments, ventilator circuits, masks, endoscopes, robotic manipulators, and stethoscopes.

When used on patients, many devices become soiled or contaminated with microorganisms. To avoid any risk of infection by a contaminated device, single use devices are discarded, and reusable devices (if approved) undergo "reprocessing." Reprocessing is a detailed, normally multi-step process, often including steps to clean, disinfect, sterilize, and dry the device.

When the labeling instructions for reprocessing are completely and correctly followed, often as directed by the US Food and Drug Administration (FDA) after each use of the device, reprocessing results in a medical device that can be safely used more than once on the same patient, or in more than one patient; thus reducing waste and expense.

Proper reprocessing of reusable medical devices is vital to protecting patient safety and is generally overseen in the United States with strict standards set by the FDA. See for example "Reprocessing Medical Devices in Health Care Settings: Validation Methods and Labeling Guidance for Industry and Food and Drug Administration Staff" (Mar. 17, 2015) by the U.S. Department of Health and Human Services, Food and Drug Administration, Center for Devices and Radiological Health Office of Office of Device Evaluation, Center for Biologics Evaluation and Research incorporated herein by reference.

Inadequate cleaning between uses can result in the retention of blood, tissue, and other biological contaminates upon and within such medical devices. The casing and any structures within the casing can allow microbes to survive the subsequent disinfection or sterilization process. These surviving contaminates could then lead to Health care-Associated Infections (HAIs). Inadequate reprocessing can also result in other adverse patient outcomes such as tissue irritation from residual reprocessing materials, for example chemical disinfectants.

FDA's evaluation of available information including reports from health care facilities indicates that there are ways to improve the reprocessing of reusable medical devices. For example, manufacturer instructions for cleaning and the high-level disinfection or sterilization of devices and their accessories are sometimes unclear, incomplete, difficult to obtain from the manufacturer, or impractical for the clinical environment. In some cases debris was retained in devices despite following manufacturer instructions.

In addition, the FDA continues to study the effectiveness of manufacturer repurposing instructions. This early research showed that in some instances, despite following manufacturer instructions, debris is occasionally retained in a device, especially devices with internal surfaces, folds, or other difficult to reach areas. The ability to adequately disassemble a device to clean all surfaces is highly desired. Such is the case resulting in the drying apparatus and methods disclosed herein. The FDA has taken steps to reduce the risk of infection from reprocessed reusable devices.

In one reprocessing process example using the apparatus and method disclose herein, such as shown in the highly schematic FIG. 1, the medical implement 30 is washed within a washing container 40 with a cleaning fluid 42. The cleaning fluids may comprise: rinsing fluids, detergents, water, alcohol, disinfectants, biocides, combinations thereof, and equivalents. In such a process, the cleaning fluid 42 will at least partially fill the medical implement 30 and inner spaces 34 therein. The reprocessing instructions for such implements instruct to dry the exterior surface and inner spaces 34 of the device following the washing process; however, testing of such medical devices according to the reprocessing instructions was found to repeatedly retain a portion of the cleaning fluid, likely containing some biological matter therein. Retention of such cleaning fluids may result in contamination of the implement 30 and further lead to infection of the next patient to be treated with the contaminated medical implement 30. Thus, the drying apparatus 20 disclosed herein was conceived to more easily and more thoroughly dry the interior space 34 of one or more medical implements 30.

Figure 2:
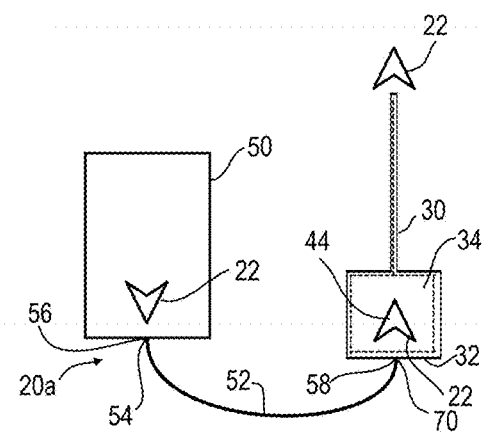

Looking to FIG. 2 is shown a highly schematic example of a drying system 20a utilizing a drying gas source 50 configured to create an airflow 22 of drying gas 44. The drying gas source 50 pumping drying gas 44 through a conduit 52 having a first end 54 attached to an outlet port 56 of the drying gas source 50 and a second end 58 attached to an inlet port 32 on the medical implement 30. In one example, the second end 58 of each conduit 52 comprises a quick disconnect coupling 70 for removable attachment of each conduit 52 to the inlet port 32 of the medical implement 30. In some examples, it is desired to include a plug 72 to close off any additional fluid ports to advantageously direct the airflow 22 within the inner space 34. While other gasses may be used, for ease in description the terms air and airflow will be used to refer to the drying gas 44.

The inlet port 32 in one example is a fluid conduit into the interior space 34 of the medical implement 30. Thus, the airflow 22 of drying gas 44 carries evaporated water and water vapor out of the interior space 34 of the medical implement 30. The drying gas 44 travels from the drying gas source 50 through the conduit 52 into the interior space 34 of the medical implement 30 and exits at an outlet port 37, the forced drying gas 44, evaporated cleaning fluid, cleaning fluid vapor, liquid cleaning fluid, and other contaminates from within the interior space 34 as the airflow 22 of drying gas dries the interior space 34.

Figure 3:
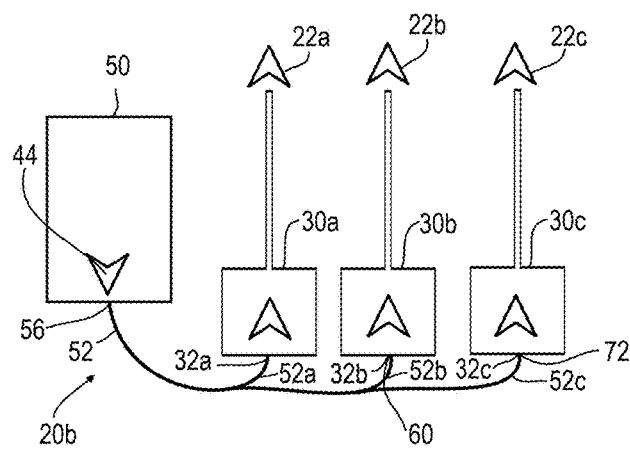
FIG. 3 is a highly schematic view of a plurality of the medical implement shown in FIG. 1 attached to a gas source via a plurality of gas conduits.

Looking to FIG. 3 is shown an alternate example of the medical implement drying apparatus 20b wherein a gas manifold 60 is connected to the conduit 52. The gas manifold 60 of this example comprises separate gas conduits 52a-52c fluidly extending between the gas manifold 60 and the inlet ports 32a-32c. This arrangement shown in FIG. 3 allows for the inner spaces 34 of multiple medical implements 30a-30c to be dried simultaneously via a single drying gas source 50.

Figure 4:
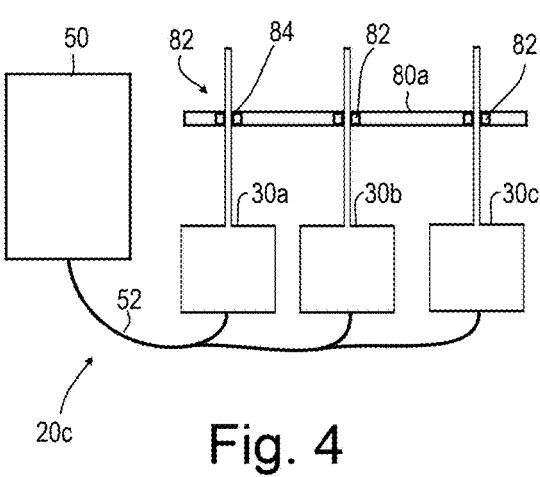
FIG. 4 is a highly schematic view of a plurality of the medical implement shown in FIG. 1 attached to a gas source via a plurality of gas conduits utilizing an implement holder component.

Looking to FIG. 4 is shown an apparatus similar to that shown in FIG. 3, with the addition of an implement rack 80a. The implement rack 80a of this example comprising attachment locations 82 which receive a portion of the medical implement 30 and attach each medical implement 30 to the implement rack 80a. In one example, this attachment is accomplished without tools by frictionally engaging opposing outer surfaces of each medical implement 30. As shown, this example of the attachment locations 82 comprises a plurality of attachment locations or coupling devices 84 which frictionally engage opposing surfaces of the medical implement 30 and retain the medical implement 30 on the implement rack 80.

FIG. 5 shows a more detailed view of another example of a support rack 80b. This example comprises an implement holder assembly 90 similar to the coupling devices 84 disclosed above, with a more specific frictional engagement. The implement holder 90 of this example comprising coupling devices 84. Each coupling device 84 configured to hold at least one medical implement 30.

This example of an implement holder 90 comprising an attachment structure 92 allowing for removable attachment of the implement holder 90 to a mounting bracket 100. The mounting bracket 100 fixed to a support structure 102 such as a wall, interior surface of a cabinet as shown in FIG. 10, support post, etc. This arrangement facilitating easy loading of the medical implements 30 on to the implement holder 90 prior to attachment of the implement holder 90 onto the bracket 100. This arrangement using an implement holder 90 and mounting bracket 100 allows for much easier placement of a plurality of medical implements 30, especially when the arrangement is used within a cabinet 150 as the interior space of such a cabinet restricts ease of access to the devices holding the implements 30. The cabinet 150 of this example being an enclosed or substantially enclosed space in which the humidity, heat, and airflow may be precisely controlled independent of the ambient air outside of the cabinet 150.

Looking to FIG. 6 can be shown a particular example comprising a plurality of implement holders 90a and 90b. In this example, the first implement holder 90a is mounted to the bracket 100 and the second implement holder 90b is mounted to the first implement holder 90a. As is conceived in this example, additional implement holders 90 may be attached to previously supported implement holders 90 in a stacking arrangement. Thus a cabinet 150 may be easily loaded with multiple implement holders 90, each holding multiple medical implements 30, wherein each mounting bracket 100 supports one or more implement holders 90.

One example of such a stacking arrangement is shown in FIG. 10 wherein the support rack 80b comprises a first implement holder 90a and a second implements holder 90b wherein the mounting bracket 100 is attached to an interior wall 152 of the cabinet 150. In this example, the door 156 is shown transparent such that the devices and structures therein can be more easily seen.

In addition to the support rack 80b, a control interface 180 is shown in FIG. 10 and in FIG. 13. The control interface 180 having a plurality of switches or other user manipulated actuators 182 such as pushbuttons or rocker switches which allow a user to control airflow, temperature, humidity, lighting etc. within the cabinet 150. The control interface 180 may also utilize circuitry, and optionally a timer readout 184 showing to a user the elapsed or remaining time of a drying sequence as well as other options. In addition, the control interface 180 may comprise visual indicators 183 to display operational status such as power, system pressure, timer, and airflow selections; these may be LED lights or equivalents.

FIG. 13 also shows a coupling 186 having a conduit 188 extending therefrom. The conduit 188 may be connected to the gas source 50, to a power supply providing power to the control interface 180, air source 50, cabinet lighting, and a drying apparatus 220. The drying apparatus 220 known in the art to remove water vapor from the interior space of the cabinet 150, thus facilitating drying of medical implements or other structures contained therein. The drying apparatus 220 may also comprise an external fan, circulating air within the cabinet 150 for more efficient heating and drying.

For efficient operation, the control interface 180 may also comprise sensors. These sensors detecting the temperature, humidity, pressure etc. within the cabinet 150 or of the drying air 44 of the airflow 22 previously described. The sensors connected to circuitry and a visual and/or audible signal, thus signaling to the operator or otherwise controlling the drying apparatus 220 and or air source 50 dependent upon the conditions detected. For example, the timer 184 may indicate to a user that insufficient time has elapsed in the drying sequence.

FIGS. 13, 14, 16 also show a plurality of endoscope holders 188 (188a and 188b). These endoscope holders in this example mounted to the outer surface of the control interface, optionally with a fastening structure that does not require the use for tools for fastening and release of the endoscope holders 188 to the supporting structure. Endoscopes are one particular type of surgical instrument and these holders are well-suited not only to endoscopes but other medical instruments as well such as for example stethoscopes. In such an example, the endoscope or other medical implement is supported on a U-shaped support surface 190 (190a, 190b) and hangs therefrom. Such implements generally having a flexible tubing section or flexible cord section which is easily looped over or around the support surface 190 and hangs therefrom. In one example, the support surface 190 is padded such as by a malleable material. In one form, neoprene is utilized. In one form, the endoscope holders 180 are supported by way of a plurality of arms 192 (192a, 192b) attached to the control interface 180. In other examples the arms 192 are mounted at other locations.

Looking again to the example of FIG. 5 in more detail, it can be seen that the implement holder 90 comprises an inlet manifold 94 having an inlet 96 coupled by way of the supply conduit 154 previously described, and extending from the air source 50 or control interface 180. The inlet manifold 94 furthermore having a plurality of manifold outlets 98 (98h) coupled to the gas conduits 52 (52a-e-52h). Gas conduits 52 each connected to the inlet ports 32 (32d-32h) of the medical implements 30 (30d-30h) respectively. In this example, the implement holder 90 can be attached to the bracket 100 within the cabinet 150 or associated device, and following this attachment, the supply conduit 154 may be attached to the inlet 96 such that independent attachment to each of the medical implements 30 need not be accomplished within the cabinet. In another example, attachment of the implement holder 90 to the bracket 100 simultaneously aligns and connects the inlet 96 to the supply conduit 154 in a single action.

In the example of FIGS. 5-7 and 10, it can be seen that the attachment structure 92 comprises a slot or bracket attachment surface 99 formed in the implement holder 90 such that the implement holder 90 simply need be dropped onto the mounting bracket 100 to be held in place by way of gravity. The attachment structure 92 in this way further prevents rotation in a vertical or horizontal plane of the implement holder 90 relative to the mounting bracket 100 when so attached.

To facilitate attachment of multiple implement holders 90 thus forming a support rack 80 holding several medical implements 30, each implement holder 90 may comprise a lateral extension 108. In example shown, the lateral extension 108 positions the implement holders 90 laterally outward of the attachment structure 92 of each implement holder 90. In this way, subsequent implement holders 90b may be attached to previous implement holders 90a in a stacking arrangement as shown in FIG. 10. In one example, each of the implement holders 90 (90a, 90b) is substantially identical and therefore multiple implement holders 90 may be mounted on a single mounting bracket 100.

Looking to FIG. 7 and to FIG. 8 the coupling devices 84 can be seen in one particular example, each coupling device 84 comprises a malleable material. In this example, the medical implement 30 is held against upper contact point 86, opposing contact point 87, and lower contact point 88. In one form, the coupling devices 84 are each attached to the implement holder 90 by way of fasteners 110.

Looking to FIG. 9, it can be seen that in this orientation the implement holder 90 is not supported by the attachment structure 92 but rests upon a horizontal surface 104 such as a table or equivalent resting surface. In this position, the coupling devices 84 open upwards and thus medical implements 30 may be easily inserted therein or alternatively, removed therefrom vertically while the implement holder 90 rests in a position where the coupling devices 84 are easily accessed. As shown, in this loading orientation, a loading surface 106 of the implement holder 90 rests upon the horizontal surface of the table 104 or equivalent. Once loaded, the implement holder 90 with medical implements 30 attached thereto may be repositioned to the holding orientation such as shown in FIG. 11 wherein the implement holder 90 is supported by the bracket 100 or alternatively another implement holder 90 in a cascading mount arrangement as previously described.

Although the drying gas source (tank, pump, or compressor) 50 may be mounted within the cabinet 150, testing has shown that the arrangement shown in FIG. 24, with the drying gas source 50a external of the cabinet 150 has the advantage that the drying gas source 50 is not subjected to the high temperatures often found in the interior of such drying cabinets 150. Such high temperatures have been known to impede performance of drying gas pumps, compressors, etc.

FIGS. 19-22 show other views of the gas source 50 mounted to the cabinet 150 by way of fasteners which may pass through malleable feet 62 mitigating vibration between the drying gas source 50 and the cabinet 150. In addition, signal and power connection through conduit 188 is connected via coupling 64 to the drying gas source 50.

In the Example of FIG. 19-22, air or other drying gas 44 may enter the drying gas source 50 through inlet 66, then compressed or pumped by way of a compressor or other pump apparatus there within, and exit from the drying gas source 50 via exit fitting 68 to conduit 158. Conduit 158 in one example fluidly coupled to control interface 180 previously described, and in another example fluidly coupled to conduit 158 coupled in turn to conduit 154 previously described.

Figure 18:
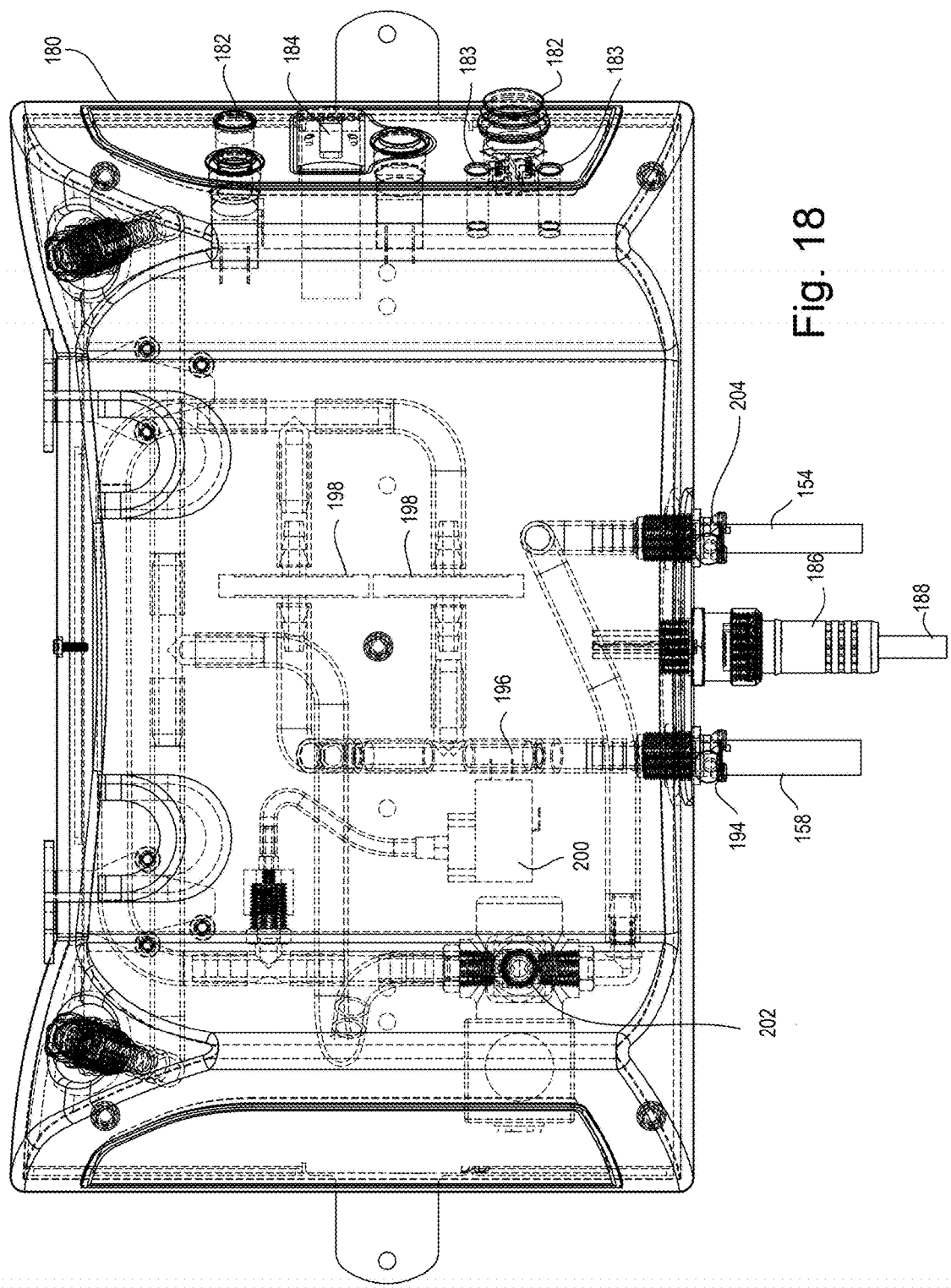

Looking to FIG. 18 is shown a hidden line view of one example of the control interface 180. In this example, the outlet fluid conduit 158 leads to an inlet 194 which in one example is a quick disconnect fitting. Many different quick disconnect fittings that would work well are-known in the art. The conduits 196 there within in one example are fluidly connected to a filter or filters 198. These filters 198 may be HEPA filters for filtering out contaminants especially microorganisms which could otherwise contaminate the interior space of the medical implements 30.

A pressure sensor 200 may be provided within the control interface 180. The pressure sensor 200 sensing air pressure through the internal conduits 196 to ensure that drying gas 44 is continuously provided therein. To facilitate continuous and even flow of drying gas 44, a valve 202 or equivalent structure may also be utilized. Downstream of the valve 202 in one example is an outlet 204 with fluid conduit 154 attached thereto. The fluid conduit 154 previously described as being attached to the medical implement 30 either directly or via a manifold such as the manifold 94.

FIG. 23 shows one example of a grommet 240 having a plurality of surfaces defining voids 242 and 244 therein. Conduits 158 and 188 in one example pass though this grommet as they enter the cabinet 150.

The examples shown above such as FIG. 6 include at least one example where several independent actions must be performed to enable drying of the medical implements using the disclosed apparatus. These steps may include for example: attachment of the medical implements 30 to the coupling devices (82, 84), connecting drying gas conduits 52 to the inlet ports 32 of the medical implements 30, connecting the implement holder 90 to a mounting bracket 100, etc.

To improve efficiency, examples are disclosed (FIG. 25-37) herein where the action of coupling the medical implement 30i to the mounting bracket also connects the gas conduit to the inlet port of the medical implement. Similarly, examples are shown where the action of attaching the implement holder to the mounting bracket also connects the drying gas manifold to the supply conduit extending from the drying gas source. These two adaptations shown in several examples below improve efficiency of the device.

Figures 25, 26:
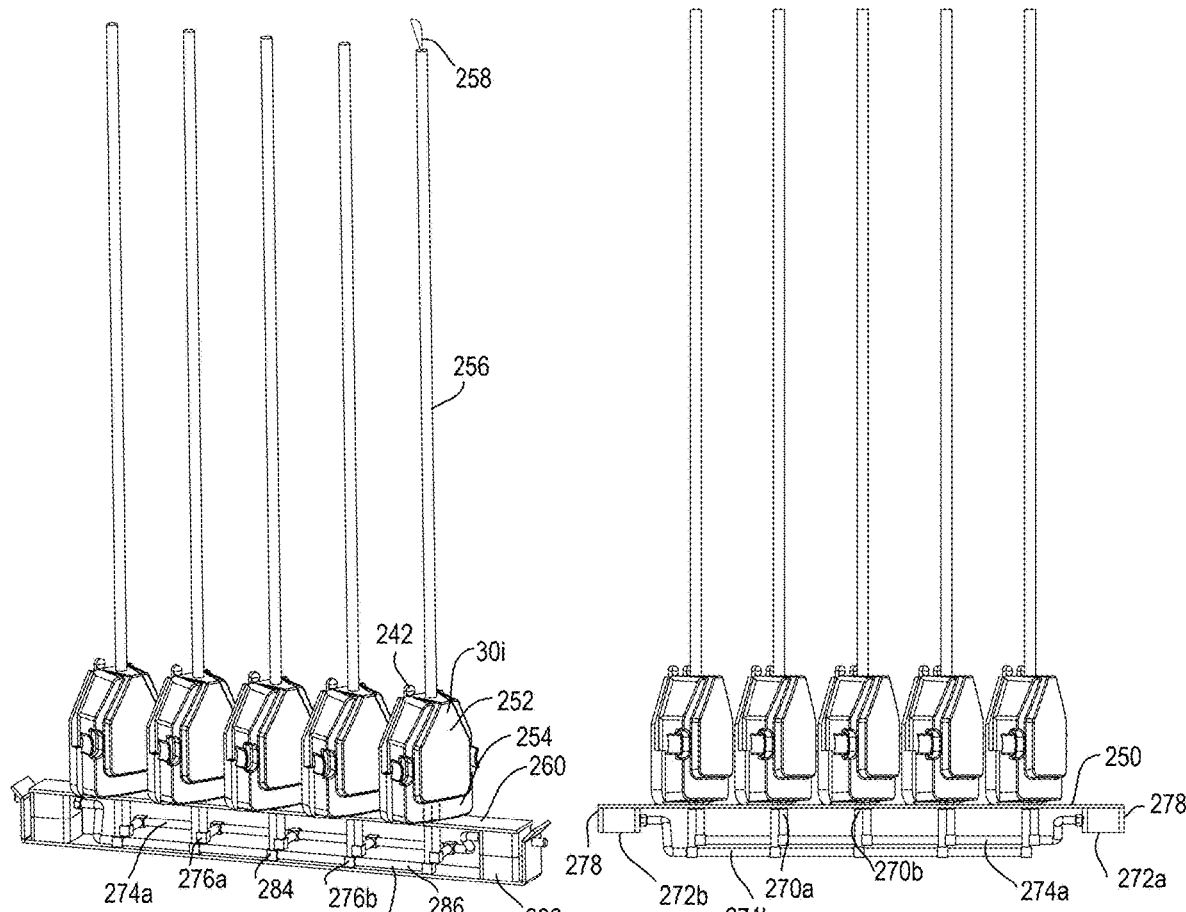
FIG. 25 is a front perspective view of another example of an implement holder with a plurality of medical implements held thereon.
FIG. 26 is a front perspective view of the example shown in FIG. 25 from a different angle.

Looking to FIG. 25 for example is shown another example of an implement holder 250 with a plurality of medical implements 30i mechanically and fluidly connected thereto. In this example, and others, each medical implement 30 has a housing 252. Each housing 252 may comprise a first portion 254 having a plurality of tool manipulating mechanisms and/or electric components therein. These mechanisms and/or electrical components are connected through the housing 252 to a robotic mechanism for use in surgical procedures as is well known in the art. Each medical implement 30 of one example having a second portion 256 forming an elongate lumen connected to the first portion 254 and extending therefrom. The lumen 256 may enclose actuators (generally fibers such as string, wires, or cables) for manipulation of a tool 258 such as a medical clamp, cutting tool, suction tool, etc.

The generally irregular inner surface of the inner space 34 of the medical implement housing 252 and components therein are known to retain fluids including cleaning fluids and other contaminates during washing and drying using conventional processes.

In the example shown in FIG. 25, an implement holder 260 is shown with novel attachment of the medical implements 30, and a novel attachment to a mounting bracket 262. The implement holder 260 is functionally similar to the implement holders (80, 90) previously discussed as holding a plurality of medical implements 30 onto a supporting structure. On significant difference is that the implement holder 260 when combined with the mounting bracket 262 as shows reduces the steps necessary for physical, fluid, mechanical, and electric connection.

Figure 27:
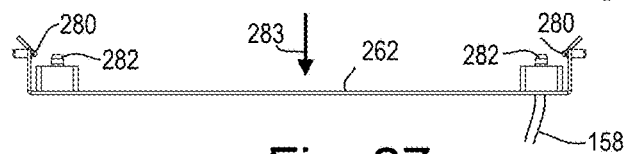
FIG. 27 is a front view of another example of a mounting bracket.

The implement holder 260 also useful for simultaneous attachment of a plurality of medical implements 30 to a mounting bracket 262 shown in FIG. 25 and shown separate from the implement holder 260 in FIG. 27. In use, a plurality of medical implements 30 may be attached to the implement holder 260, and then the implement holder 260 is attached to the mounting bracket 262 where physical and fluid connections may be simultaneously made.

The implement holder 260 shown in these examples includes a coupling device 264 to physically receive and mount each medical implement to the implement holder. This example of an implement holder 260 is similar in some ways to the coupling devices (82, 84) previously described with a different approach to physical attachment and fluid connection.

These coupling devices 264 in this example comprising a plurality of alignment protrusions 266 (266a, 266b) which engage notches 268 or grooves, or dovetails, in the housing 252 of the medical implement 30i. When in use for surgical or other medical procedures, the medical implement 30i is attached and secured to a robotic device using these notches 268. The notches 268 align and connect the medical implement 30i to the robotic device and may be used in combination with other surfaces to make physical, mechanical, electronic, and fluid connections. The mechanical and electronic connections used to manipulate the tool 258.

One advantage of attachment of the medical devices 30i to the implement holder 260 via the notches 268 is that the sliding movement 269 of engaging the medical implement 30 on to the coupling device 264 via the alignment protrusions 266 moves the medical implement 30 substantially parallel to the axis of the inlet ports 32i. Thus, the fluid connectors 270 (270a and 270b of FIG. 26) may be positioned on the implement holder 260 relative to the alignment protrusions 260 wherein mounting of the medical implement (s) on the coupling device 264 also engages the fluid connector(s) 270 to the inlet port(s) 32i of the medical implements 30i. Thus, physically connecting the medical implement 30 to the implement holder 260 simultaneously connects the fluid conduits there between with the same engagement action.

FIG. 25 also shows an example where the implement holder 260 comprises at least one inlet port 272 (272a, 272b) which are connected via a manifold 274 (274a and 274b) to fluid connections 276 (276a and 276b). These fluid connections 276 connect to inlet ports 32i on the medical implement 30 and thus provide a fluid conduit from the inlet port 272 to the inner space 34 of each medical implement 30.

Fluids, including cleaning fluids and drying fluids flow into the inner space 34 via this conduit, and generally exit via gaps in the housing 252 such as at the tool 258.

Looking to FIG. 26 is shown a plurality of detents 278 on the implement holder 260. These detents engage protrusions 280 on the mounting bracket to physically retain the implement holder 260 with medical implements 30 on the mounting bracket 262.

Similarly, the mounting bracket 262 comprises at least one fluid connector 282 configured to form a fluid connection to the inlet port 272 of the implement holder. Each fluid connector 282 coupled to a cleaning fluid source or the drying gas source 50 as previously described. As the implement holder 260 is attached to the mounting bracket 262 in direction of travel 283, fluid connections 272/282 and physical connections 278/280 are simultaneously made.

In one example, each mounting bracket 262 is fixed to a support structure, such as the interior wall 152 of a drying cabinet 150.

In one example, restrictors 284 are utilized upstream of each fluid connector 276. Thus, the manifold 286 can be specifically configured for a particular model of medical implement 30. For example, a restrictor 284 may be configured to allow a volume of fluid there through dependent upon the restrictions within the medical implement 30. For example, a medical implement 30 having a small flow-through passage for a specific inlet 276 may be provided with a small opening restrictor 284, thus reducing the forces on the medical implement 30 which may otherwise tend to force the medical implement 30 off of the implement holder 260.

Figure 28:
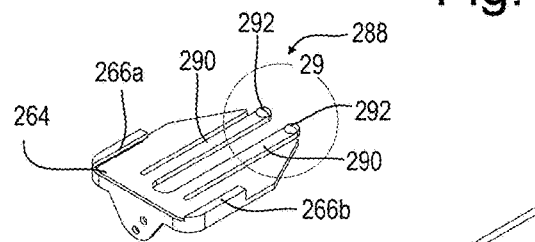
FIG. 28 shows another example of a coupling device component.
Figure 30:
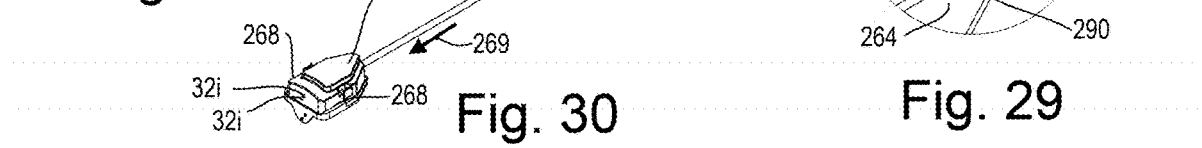
FIG. 30 is a perspective view of one example of a medical implement held by a coupling device as shown in FIG. 25.
Figure 29:
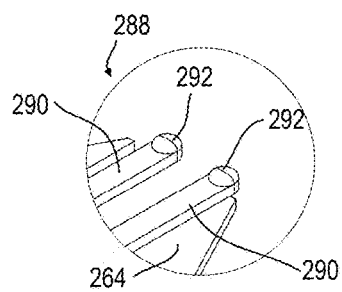
FIG. 29 is an enlarged view of the region 29 of FIG. 28.

Looking to FIG. 28 and the enlarged detail view of FIG. 29, it can be seen that in one example the coupling device 264 comprises a retaining mechanism 288. In this example, the retaining mechanism comprises one or more cantilevered elastic arms 290 having a protrusion 292 on the end thereof. The protrusion 292 engaging a portion of the medical implement 30 as can be seen in FIG. 25.

Looking to FIG. 31 is shown another example of a plurality of coupling devices 300 which when mounted to an implement holder 302 retains the medical implements 30 (30d-30h). As with the example shown in FIG. 25-29, each coupling device 300 is configured that the medical implement is received by the coupling device 300 in a direction 304 generally aligned that connectors 306 (306a and 306b) connect with the inlet ports 32 of the medical implements. Connectors 306, 276, 52 may insert partially into the ports 32 of the medical implement 30 or may fit against the surfaces there such as an O-ring or similar structure forming a loose seal or tight seal thereto. Thus, when the medical implement 30 is mechanically attached to the coupling device 300, the fluid connections are simultaneously made. Thus, physically connecting the medical implement 30 to the implement holder 302 simultaneously connects the fluid conduits there between with the same engagement action.

As shown, a plurality of medical implements 30 (30d-30h) are thus attached to the implement holder 302 which then may be mounted to a mounting bracket 308. The mounting bracket 308 similar or identical to the mounting bracket 262 previously described.

Thus, physically connecting the medical implement 30 to the implement holder 302 simultaneously connects the fluid conduits there between with the same engagement action.

FIG. 36 also shows an example where the implement holder 302 comprises at least one inlet port 310 (310a, 310b) which are connected via a manifold 312 (312a and 312b) to fluid connections 306 (306a and 306b). These fluid connections 306 connect to inlet ports 32 on the medical implement 30 and thus provide a fluid conduit from the inlet port 310 to the inner space 34 of each medical implement 30.

Fluids, including cleaning fluids and drying fluids flow into the inner space 34 via this fluid conduit, and generally exit via gaps in the housing 314 such as at the tool 3416.

In the example shown here, the coupling device 300 comprises first arms 316a and 316b which engage a first surface 318 of the medical implement 30, and at least one arm 318 which contacts an opposing surface 320 of the medical implement 30. In this example, the arms 316 and 318 conform to the surfaces of the medical implement 30. To improve cleaning and drying accessibility to the surfaces of the arms 316 and 318 may be configured for point contact, thus reducing any pooling of fluids on the surfaces of the medical implement 30.

Looking to FIG. 31, and the enlarged detail view of FIG. 33, it can be seen that in one example the coupling device 300 comprises a retaining mechanism 324. In this example, the retaining mechanism 324 comprises one or more cantilevered elastic arms 326 having a protrusion 328 on the end thereof. The protrusion 328 engaging a portion of the medical implement 30 as can be seen in FIG. 31 so as to retain the medical implement 30 on the coupling device 300. The retaining mechanism 324 having sufficient resiliency to overcome pressure on the connectors 306 which may otherwise tend to force the medical implement 30 away from the connectors 306.

While the present invention is illustrated by description of several embodiments and while the illustrative embodiments are described in detail, it is not the intention of the applicants to restrict or in any way limit the scope of the appended claims to such detail. Additional advantages and modifications within the scope of the appended claims will readily appear to those sufficed in the art. The invention in its broader aspects is therefore not limited to the specific details, representative apparatus and methods, and illustrative examples shown and described. Accordingly, departures may be made from such details without departing from the spirit or scope of applicants' general concept.

The invention claimed is:

1. A medical implement drying apparatus comprising:
a drying gas source;
at least one gas conduit fluidly connecting the drying gas source to a medical implement having an inner space defined by a housing comprising a tool manipulating mechanism;
the mechanism connected through the housing to a robotic mechanism configured for use in surgical procedures;
the medical implement comprising a second portion forming an elongate lumen connected to the first portion and extending therefrom;
the elongate lumen further defining the inner space;
the lumen enclosing actuators configured for manipulation of a surgical tool configured to be inserted and manipulated within a patient;
the drying gas source fluidly coupled to the inner space of the medical implement;
the housing of the medical implement having an inlet port coupled to the gas conduit in fluid communication with the inner space of the medical implement;
the gas conduit removably attached to the inlet port; and
wherein the medical implement drying apparatus is configured such that drying gas flows from the drying gas source, through the gas conduit into the inner space, absorbs liquid, from within the medical implement, to expel the liquid from the medical implement.

2. The medical implement drying apparatus as recited in claim 1 further comprising:
a gas manifold having an inlet coupled to the drying gas source and a plurality of manifold outlets;
each manifold outlet independently coupled to at least one of the gas conduits;
a plurality of the medical implements; and
each medical implement simultaneously, removably coupled to the gas manifold via at least one of the manifold outlets.

3. The medical implement drying apparatus as recited in claim 1 further comprising:
an implement rack;
the implement rack comprising a plurality of attachment locations; and
each attachment location configured for simultaneous attachment and retention of a separate medical implement.

4. The medical implement drying apparatus as recited in claim 3 further comprising:
a drying gas manifold having an inlet coupled to the drying gas source and a plurality of manifold outlets;
a plurality of the medical implements;
each medical implement simultaneously and independently coupled to the gas manifold via an associated gas conduit coupled to the gas manifold; and
wherein the manifold outlet is fixed to the implement rack and removably coupled to the drying gas source.

5. The medical implement drying apparatus as recited in claim 3 further comprising:
a mounting bracket fixed to a support structure; and
the implement rack removably attached to the mounting bracket.

6. The medical implement drying apparatus as recited in claim 5 wherein the implement rack comprises:
a first implement holder comprising a plurality of attachment locations;
the first implement holder removably supported by the mounting bracket;
a second implement holder comprising a plurality of attachment locations; and
the second implement holder removably supported by the first implement holder.

7. The medical implement drying apparatus as recited in claim 6, each implement holder comprising:
an inlet manifold having an inlet coupled to the drying gas source and a plurality of manifold outlets;
each manifold outlet coupled to at least one of the gas conduits; and
each medical implement coupled to the inlet manifold via at least one of the gas conduits.

8. The medical implement drying apparatus as recited in claim 6, each implement holder comprising:
a loading surface wherein the loading surface is configured to rest on a support surface in a loading orientation as medical implements are removably held by the implement holder; and
a bracket attachment surface configured to removably attach the implement holder to the mounting bracket without tools in a holding orientation.

9. The medical implement drying apparatus as recited in claim 8 wherein the loading orientation is substantially orthogonal to the holding orientation.

10. The medical implement drying apparatus as recited in claim 1 comprising:
a substantially enclosed cabinet;
the cabinet closing, each gas conduit, each medical implement;
the drying gas source external of the cabinet; and
a supply conduit in fluid communication with the drying gas source and each gas conduit.

11. The medical implement drying apparatus as recited in claim 9 comprising: a drying apparatus configured to reduce the humidity within the cabinet.

12. The medical implement drying apparatus as recited in claim 9 comprising: a control interface mounted to the cabinet wherein the control interface comprises user manipulated actuators configured to control airflow through the supply conduit.

13. The medical implement drying apparatus as recited in claim 10 wherein the control interface comprises a timer visually observable to an operator.

14. The medical implement drying apparatus as recited in claim 9 wherein the drying gas source has in inlet port exterior of the cabinet.

15. The medical implement drying apparatus as recited in claim 1 wherein the liquid comprises a cleaning liquid.

16. The medical implement drying apparatus as recited in claim 15 wherein the cleaning liquid is water.

17. The medical implement drying apparatus as recited in claim 1 wherein the medical implement is a robotic assembly previously used in a remote surgical processes.

* * * * *